United States Patent [19]
Brite

[11] Patent Number: 5,141,707
[45] Date of Patent: Aug. 25, 1992

[54] SCENT DISPENSING AIR REGISTER

[76] Inventor: Deric L. Brite, 1430 Newcastle Rd., A-1, Durham, N.C. 27704

[21] Appl. No.: 733,672

[22] Filed: Jul. 22, 1991

[51] Int. Cl.$^5$ ................................................ A61L 9/00
[52] U.S. Cl. ..................................... 422/124; 454/290
[58] Field of Search ......................... 239/55, 57, 60; 422/123, 124; 454/284, 289, 290, 291, 309

[56] References Cited

U.S. PATENT DOCUMENTS

| | | | |
|---|---|---|---|
| 1,091,929 | 3/1914 | Hammesfahr | 422/124 |
| 1,183,746 | 5/1916 | Lesh | 454/291 |
| 2,234,021 | 3/1941 | Castrique | 422/123 X |
| 2,778,678 | 1/1957 | Shields et al. | 422/124 |
| 3,747,742 | 3/1974 | Clark et al. | 239/57 |
| 4,338,859 | 7/1982 | Claytor | 454/291 |
| 4,523,870 | 6/1985 | Spector | 239/57 X |
| 4,903,584 | 2/1990 | Styles. | |

Primary Examiner—Harold Joyce
Attorney, Agent, or Firm—Olive & Olive

[57] ABSTRACT

An air distribution register which includes an odorant substance container positioned in a central area beneath the top surface of the register. The odorant container has holes in its bottom, ends and side surfaces for air circulation therethrough. A fragrance producing substance is placed into the container by opening a hinged cover. The application of the desired odor can thus be accomplished separately for each room in the air distribution system.

6 Claims, 2 Drawing Sheets

SCENT DISPENSING AIR REGISTER

FIELD OF THE INVENTION

The invention disclosed herein relates to the field of conditioned air distribution systems, and more particularly to air outlet registers.

BACKGROUND OF THE INVENTION

A large proportion of the homes in use and being built today have heating and air conditioning systems utilizing air as the medium of distributing temperature conditioned air throughout the building. The use of air for this function is popular because air is inexpensive, efficient, and universally available.

One significant drawback in the use of air for the distribution of heat or coolness is that the air used for conducting the desired temperature is also capable of conducting unwanted characteristics. A frequently occurring and disliked characteristic which the air in such a system may carry is that of unpleasant odors. If one of the rooms which is served by the air distribution system contains a strong odor, that odor is in the air and will be conducted through the system to all other locations in the building.

Many pleasant smelling fragrances are sold on the market today which are intended to improve the odor conditions within a room or other building space. Usually these odorants are placed in a spot from which the odorant broadcasts its pleasant smell such that the closer one is to the source, the stronger the smell seems to be. As with unwanted foul smells, the pleasant smell will be picked up by the air system and distributed throughout the house, but will always be strongest in the area of origination.

An alternate method of improving the odor in a room is by the use of a liquid chemical substance which is sprayed into the air by means of pressure. The spraying method improves the movement of the smell to a greater area according to the direction and power of the propellant, but it lasts for only a short time.

The present invention recognizes that if an air distribution system can function to spread foul odors throughout a building the same system could be utilized to distribute desirable odors.

Therefore, it is an objective of the present invention to provide a building odor improving system which continuously improves the odor in a building.

It is also an objective of the present invention to provide a system which is variable and can modify the odor conditions primarily in certain rooms.

It is an additional objective of the present invention to provide a building odor improving system which distributes an odor improving fragrance uniformly over a large area.

It is a further objective of the present invention to provide a building odor improving system to function in an existing air distributing heating and air conditioning system.

These and other objectives will become apparent as the present invention herein is disclosed.

SUMMARY OF THE INVENTION

The invention disclosed herein provides an air distribution register having an enclosure for storing a substance capable of producing a desirable odor. The enclosure is positioned in the air stream passing through the register and has air passages to carry the air into direct contact with the fragrant substance and then to distribute its odor throughout the room or rooms so equipped. This invention effectively creates an air odor modification system which broadcasts continuously and distributes uniformly. Use of the Scent Distributing Air Register may be restricted to one room in a system or spread to all the rooms.

DESCRIPTION OF THE PREFERRED EMBODIMENT

Figure 1:
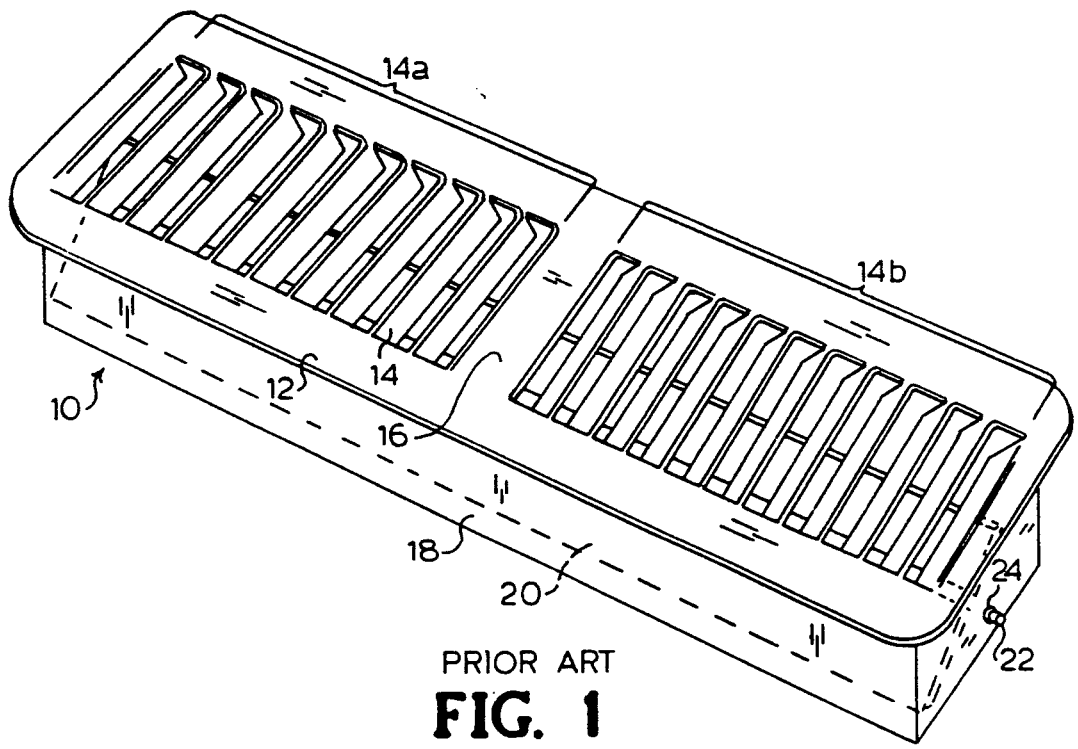
FIG. 1 is a perspective view of a prior art air distribution register as is commonly known.

In most homes and commercial buildings in which the temperature is controlled and air is used as the distribution medium, registers are used at the point where the air is released into a room. A typical configuration of an air register as it exists in the prior art is illustrated in FIG. 1. Register 10 is placed in fluid communication with the distal end of an air distribution duct (not shown) and is mounted with upper plate 12 parallel to and in contact with a floor, wall, or ceiling within the room being served.

Upper plate 12 of register 10 has a series of air outlet flow vanes 14 which define air passage ways and which are divided into two sets 14a, 14b. Sets 14a, 14b of flow vanes 14 differ in that they are directed away from each other, each set directing air flow toward the left and right ends of upper plate 12, respectively. In this manner, air flowing through register 10 is dispersed as it enters the room and is distributed broadly. Between sets 14a, 14b of flow vanes 14 is bridge 16 which contains no outlets and does not pass air through.

Permanently attached below upper plate 12 is rectangular tube 18. The air flow through rectangular tube 18 and upper plate 12 is adjustable in flow quantity by the interposition of flap 20 which is hinged at either end with axis pins 22 which pass through bearing hole 24 in the end plate of rectangular tube 18. Typically, an adjusting lever (not shown) which is connected to flap 20, protrudes through upper plate 12 to allow ease of angular adjustment of flap 20.

Figure 2:
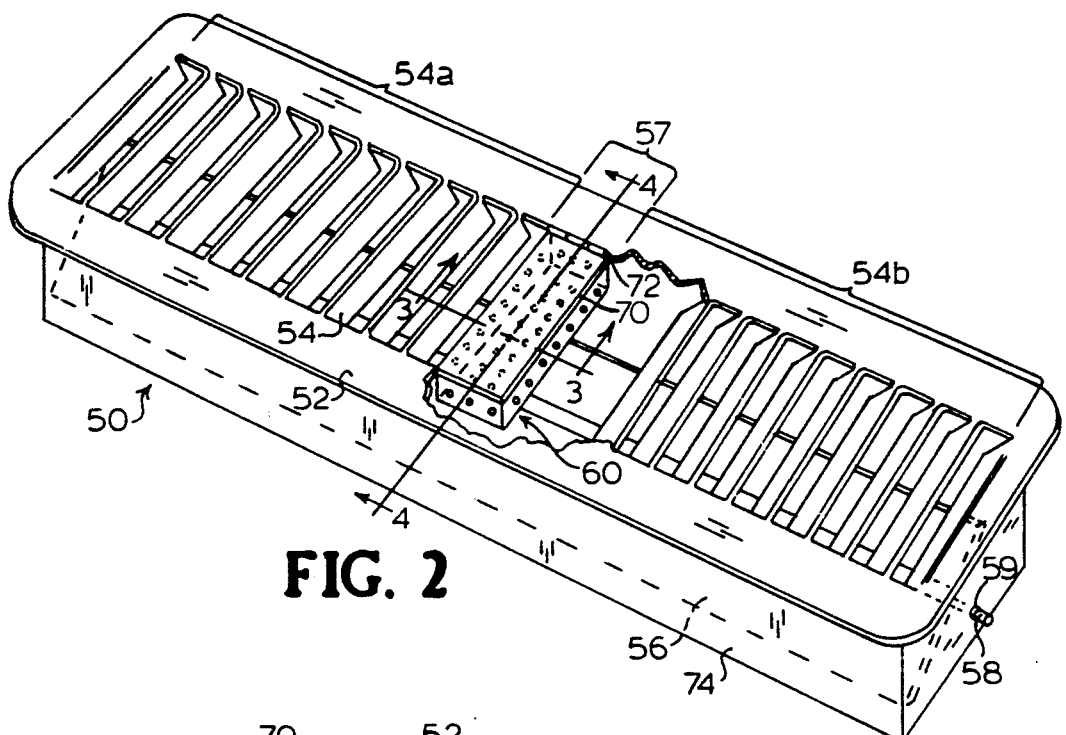
FIG. 2 is a perspective view of the register of the present invention illustrating the odorant enclosure in the middle area thereof with a portion of the register cut away for clarity.

In general outline, register 50 of the invention as shown in FIG. 2 is similar to prior art register 10 of FIG. 1. Upper plate 52 has air outlet flow vanes 54 which are divided into sets 54a, 54b facing away from the center of upper plate 52 and separated by central section 57 which has no vanes.

Rectangular tube 74 is permanently attached below plate 52. Air control flap 56 is pivotably and symmetrically mounted on axis pins 58 which extend through bearing holes 59. Air flap 56 is operable by means of an adjustment lever (not shown) to control the amount of air flowing through register 50. In some styles of register 50, particularly in wide models, there may be 2 flaps 56 for control of air flow.

The difference in register 50 of the invention over the prior art is mainly the addition of odorant container 60 residing with its cover 70 flush with, and its body below, plate 52 in central section 57. Container 60 is shown in the preferred embodiment as being a rectangular box, though the geometry could be different and the box would still fulfill the objectives of the present invention. A means of closure for odorant container 60, being in the form of rectangular cover 70, is hinge mounted so as to enable the upper opening of container 60 to be opened and closed. Hinge pin 72, placed through rolled portions of cover 70 and plate 52, permits cover 70 to be pivotably opened and the supply of odorant placed into container 60. A convenient catch (not shown) may be employed to keep cover 70 closed, especially when register 50 is to be installed in a wall or ceiling.

Figure 3:
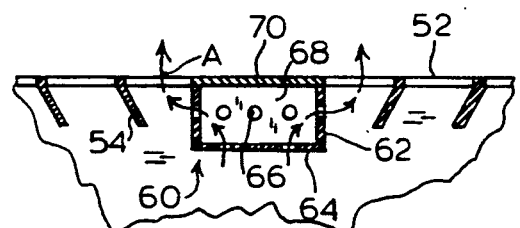
FIG. 3 is a cross sectional elevation view taken in the direction of lines 3—3 of FIG. 2 showing the odorant enclosure assembled to the upper plate of the register.

A further detail of container 60 is depicted in FIG. 3 as a sectional view taken in the direction of lines 3—3 of FIG. 2. Odorant container 60 is shown mounted by any convenient method or integrally molded below plate 52 and having cover 70. Also shown in detail in FIG. 3 are airflow vanes 54 which face opposite outward directions on either side of the container 60. Sides 62, ends 68 and bottom 64 of container 60 are formed with small apertures 66, configured so as to prevent the odor producing substance from dropping out of container 60. Apertures 66 may appear in a variety of patterns on the sides, ends, top and bottom of container 60 within the scope of the invention. Apertures 66 permit the passage of air from the air supplying duct into the room being heated or cooled according to arrows A so as to circulate a fragrance from a substance within container 60. The size, number and placement of apertures 66 are within the discretion of the designer of the register.

Figure 4A:
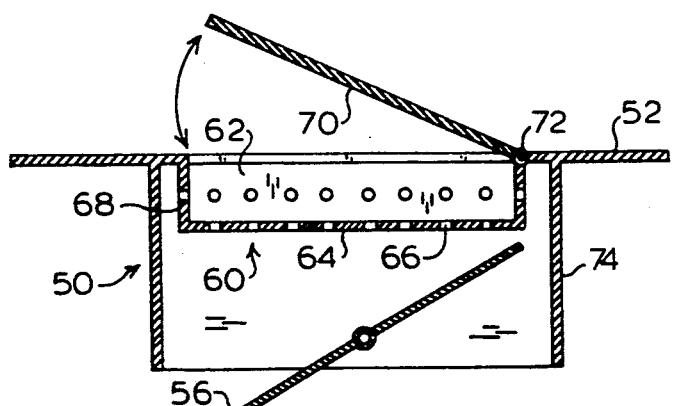
FIG. 4A is the cross sectional elevation view of FIG. 4 shown with the cover of the odorant enclosure open to enable replenishment of the odor dispensing substance.
Figure 4:
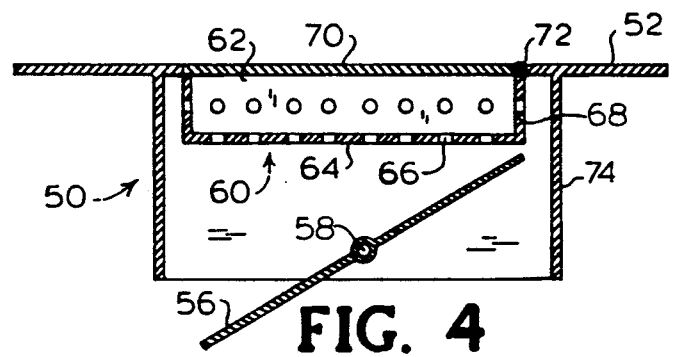
FIG. 4 is a cross sectional elevation view perpendicular to that of FIG. 3 and taken in the direction of lines 4—4 of FIG. 2 showing the odorant enclosure below the register plate with the cover of the odorant enclosure closed.

FIG. 4 shows a view of container 60 taken perpendicular to that of FIG. 3 in the direction of lines 4—4 of FIG. 2. Bottom 64, ends 68 and sides 62 have apertures 66 formed therethrough. In the preferred embodiment, cover 70 has no apertures and air flows out through holes 66 in sides 62 and ends 68. Cover 70 is configured to be opened and closed by pivoting about hinge pin 72 which is inserted through rolled portions anchored to side 68 and plate 52. Rectangular tube 74 is adapted to fit somewhat snugly into a similarly shaped air supplying duct. Air control flap 56 is pivoted around pins 58 so as to be able to angularly adjust and to regulate air flow through register 50 by means of an adjusting lever (not shown).

As is illustrated in FIG. 4A, cover 70 pivots upwardly when lifted, permitting access to the inside of container 60 so that the quantity of odor enhancing substance may be replenished. Grasping the side edges of cover 70 will permit a simple means of opening container 60. As illustrated, cover 70 will be held closed by friction with the abutting edge of plate 52 opposite hinge pin 72. In other embodiments, a catch may be added if desirable. A further possible embodiment of the invention is to adapt a perforated odorant container to be mounted on an existing air register in a heating or air conditioning system.

The embodiment depicted in the drawings and the disclosure relates to an odorant in a solid form, in particular pellets of fragrant, volatile substance. Other forms of odor improving chemical may occur to those skilled in the art, such as a liquid or a single piece solid bar. The form chosen may dictate the configuration of container 60 and apertures 66 therethrough. It is also considered an advantage of the preferred embodiment to dispense the fragrance in each room in which the invention is used rather than in a central location for the entire air distribution system. This method allows the use of odor modifying chemicals primarily in the areas where they are most needed.

A further improvement of the preferred embodiment is to produce register 50 out of plastic, rather than the conventionally used metal. The advantages offered by the use of plastic for this product are several. In household and office use the registers are usually mounted in the floor, and therefore may be prone to being damaged if scratched by furniture legs or the nails of some shoe bottoms. If the scratched register were painted metal, the damaged section would show a different color. The color of a plastic part is typically molded into the body of the item and a scratch will not be visible for lack of color contrast. Also, since these parts are somewhat decorative, a plastic part could be molded with a textured surface so as to blend visually with the carpeting adjacent to it. The plastic molded part will also not be susceptible to rusting. A large number of specific plastic resins would be appropriate to the requirements of the invention.

Whereas the objectives of the present invention have been satisfied by the disclosed preferred embodiment, it is understood that there will be additional forms of the invention apparent to those skilled in the art and which are to be considered within the scope of the invention disclosed.

What is claimed is:

1. An air distribution register for dispensing a desired odor into a room, comprising:
   (a) an upper plate having a plurality of air flow vanes positioned to define air passages and to direct the flow of air passing therethrough;
   (b) a rectangular tube supported below said upper plate and sized to slidingly fit into an air supplying duct;
   (c) an air control flap pivotably mounted within said rectangular tube and adapted for regulating the quantity of air passing therethrough; and
   (d) an odorant container mounted to said upper plate and adapted to contain an odor producing substance and capable of dispensing an odor therefrom, said odorant container comprises a rectangular container having apertures capable of passing air therethrough.

2. An air distribution register as claimed in claim 1 in which said odorant container is formed as a structure having a cover.

3. An air distribution register as claimed in claim 2, in which said cover is hingedly attached to said container so as to enable said cover to be pivotably opened and closed.

4. An air distribution register as claimed in claim 1 in which said odorant container is mounted below said upper plate.

5. An air distribution register as claimed in claim 1 in which said upper plate, rectangular tube and odorant container are made of a plastic material.

6. An air distribution register as claimed in claim 1 further comprising a fragrant volatile substance adapted to be placed into said odorant container and to dispense an odor into the air passing therethrough.

* * * * *